United States Patent
Hewett et al.

(10) Patent No.: US 8,036,434 B2
(45) Date of Patent: Oct. 11, 2011

(54) POST-PROCESSING OF MEDICAL MEASUREMENT DATA

(75) Inventors: Andrew John Hewett, Erlangen (DE); Helmut König, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1231 days.

(21) Appl. No.: 11/441,254

(22) Filed: May 26, 2006

(65) Prior Publication Data

US 2007/0008172 A1 Jan. 11, 2007

(30) Foreign Application Priority Data

May 27, 2005 (DE) .......................... 10 2005 024 326

(51) Int. Cl.
*G06K 9/00* (2006.01)
*G06Q 10/00* (2006.01)
(52) U.S. Cl. .......................................... 382/128; 705/2
(58) Field of Classification Search .................. 382/128; 705/2; 345/418
See application file for complete search history.

(56) References Cited

U.S. PATENT DOCUMENTS

| | | | | |
|---|---|---|---|---|
| 5,935,060 A * | 8/1999 | Iliff | | 600/300 |
| 6,511,426 B1* | 1/2003 | Hossack et al. | | 600/437 |
| 7,110,605 B2* | 9/2006 | Marcellin et al. | | 382/232 |
| 7,142,703 B2* | 11/2006 | Kaufman et al. | | 382/131 |
| 7,388,975 B2* | 6/2008 | Faber et al. | | 382/128 |
| 7,490,085 B2* | 2/2009 | Walker et al. | | 1/1 |
| 2003/0100820 A1* | 5/2003 | Birkhoelzer et al. | | 600/300 |
| 2004/0147840 A1* | 7/2004 | Duggirala et al. | | 600/437 |
| 2004/0152957 A1* | 8/2004 | Stivoric et al. | | 600/300 |
| 2005/0080328 A1* | 4/2005 | Vass et al. | | 600/407 |
| 2005/0097545 A1* | 5/2005 | Tarbox et al. | | 717/176 |
| 2005/0147311 A1* | 7/2005 | Faber et al. | | 382/240 |
| 2007/0109294 A1* | 5/2007 | Gotman et al. | | 345/418 |

FOREIGN PATENT DOCUMENTS

DE 10347433.1 10/2003
WO WO 2005051197 A2 * 6/2005

* cited by examiner

*Primary Examiner* — Wengpeng Chen

(74) *Attorney, Agent, or Firm* — Harness, Dickey & Pierce, P.L.C.

(57) ABSTRACT

A method and a device are disclosed for selecting at least one post-processing method for the post-processing of medical measurement data. In this method, different post-processing components are registered. In addition to the measurement data, context data with respect to the measurement data are acquired and/or derived. Following this, a structured document is evaluated so that at least one post-processing method, for example an optimally designed method, can be selected for the respective measurement data.

12 Claims, 3 Drawing Sheets

POST-PROCESSING OF MEDICAL MEASUREMENT DATA

The present application hereby claims priority under 35 U.S.C. §119 on German patent application number DE 10 2005 024 326.6 filed May 27, 2005, the entire contents of which is hereby incorporated herein by reference.

FIELD

The invention generally is in the field of post-processing of measurement data, for example measurement data in the medical/clinical environment.

BACKGROUND

In principle, there is a multiplicity of arrangements or detectors by which medical measurement data can be acquired, such as, for example, computer tomographs, nuclear magnetic resonance tomographs, X-ray devices or laboratory devices for evaluating blood samples etc. As a rule, the measurement data acquired in this way are supplied to further post-processing methods. The post-processing methods can include a display of the data acquired, or of reconstruction processes (particularly in the case of image data) or of other evaluating processes (e.g. statistical methods) or other types of post-processing methods.

The measurement data acquired in one or also in more arrangements are usually stored in particular formats. In this context, formats such as the DICOM SR Standard (Digital Imaging and Communications in Medicine, Structured Reporting), the HL7 CDA Standard (Clinical Document Architecture, this standard comprises exchange models for clinical documents, for example for discharge reports, diagnoses or other reports in the clinical environment) are known. It is based on the use of a uniform vocabulary so that the documents covered by this standard can be more easily supplied to electronic automatic processing. Similarly known is the ASTM CCR Standard (Continuity-of-Care Record). This standard developed by the ASTM (American Society for Testing and Materials) is directed towards being able to structure and transmit quickly and in a simple manner fundamental information about the health or the health development of a patient. An ASTM CCR is a digital file in XML format which is compatible with other health or clinical systems.

Once the measurement data have been acquired, there is a necessity, as a rule, for post-processing these data by further post-processing steps.

From DE 103 47 433, a method for generating result images in the medical field is known, the images being related to an object of examination, which are processed by way of a workflow in such a manner that the result images can be generated.

In the aforementioned and other known systems from the prior art, a user hitherto disadvantageously had to select a suitable post-processing method by hand. An error source in the previous systems which is not to be underestimated can be seen, therefore, in that the measurement data acquired are not processed by way of a fitting or suitable post-processing method. A disadvantage of previous systems can thus be seen in that the user receives no further instructions on how these measurement data should best be further processed.

SUMMARY

At least one embodiment of the present invention includes an object, therefore, of finding a way by which the aforementioned disadvantages can be overcome and which enables the post-processing of measurement data to be improved and to be simplified, and, in particular, to provide an optimally selected or designed post-processing method—that is also for different types and/or different combinations—of measurement data. In this context, the optimum selection or design of the post-processing method should be automatic.

An object may be achieved, in at least one embodiment, by a method for selecting at least one post-processing method for the post-processing of measurement data which are present in a predeterminable format, the post-processing being carried out by one or more post-processing components, the method comprising:

Registering post-processing components which are designed for carrying out various post-processing methods so that it is defined for each post-processing component what type of measurement data are required by it. In the process of registering it is therefore stipulated which type of input data is required for the respective post-processing method.

Acquiring and/or deriving context data with respect to the respective measurement data, parsing the measurement data enriched with the context data in accordance with the format in which the measurement data are present, evaluating the parsed data in dependence on the registered post-processing components so that an optimally designed post-processing method can be selected for the respective measurement data and selecting at least one optimally designed, particularly registered, post-processing method for the measurement data.

In an example embodiment, the measurement data are already acquired and stored in a particular—and configurable—format. As a rule, the format is based on the DICOM SR Standard. However, it is also within the context of the invention to use other standards in this case, such as, for example, the HL7 CDA Standard, the ASTM CCR Standard, the LOINC or XML Standard.

In the context of at least one embodiment of the present invention, the term "measurement data" is understood to cover all data which have been acquired by a so-called arrangement, that is to say by an acquisition device. As a rule, these are medical data in the clinical field.

However, the principle of at least one embodiment of the invention can also be transferred to other technical measurement data. The measurement data are thus acquired by sensors or other detectors and can be optionally supplied to preprocessing. The preprocessing can reside, for example, in a combination and/or selection of various data records or in a method for improving the image quality etc.

The devices by which the measurement data are acquired can be, for example, a computer tomograph, a nuclear magnetic resonance tomograph, an X-ray device or laboratory device for examining blood values or other cellular material. As a rule, these devices have interfaces for transmitting the measurement data in digital form to other entities. The measurement data thus acquired and/or transmitted are transmitted to the method according to at least one embodiment of the invention or the device according to the invention, respectively.

The aforementioned essential steps of the method according to at least one embodiment of the invention can be carried out at different times. This results in the advantage that the method according to at least one embodiment of the invention can be subdivided into different time segments and thus provides for improved utilization of system resources.

In a preceding step, in particular, the post-processing components can be registered. In this step, it is defined for each of the post-processing methods or for each of the post-processing moments, respectively, what type of post-processing and/or what post-processing steps are supported by it. Each post-processing tool, e.g. statistical tools, tools for indicating the respective data, tools for processing the data by user interactions etc., requires a different input, that is to say a different type of measurement data (the term "tool" is in this case understood to be synonymous with the term "component"). In the case of functional imaging (e.g. PET data), for example, a tool for the two-dimensional representation of measurement data in the form of a diagram (which is suitable for measurement values) does not make any sense. The selection of an unsuitable post-processing tool can thus completely falsify the measurement data originally acquired correctly and render them useless overall.

According to at least one embodiment of the invention classes or categories of measurement data are generated, a group of post-processing methods or post-processing tools respectively (in the form of components) being allocated for each measurement data class. According to at least one embodiment of the invention, the selection of a wrong, unsuitable or of a non-optimally designed post-processing method for the respective measurement values is impossible. In particular, this allocating process takes place in the method step of registering. This can precede the other steps in time.

In addition, it is possible to make the method dynamic and adaptively to supply further post-processing components to the method. This is possible in that the user, even after application of the method according to at least one embodiment of the invention, introduces further post-processing components by registering these. The method according to at least one embodiment of the invention can thus be adapted dynamically to the respective application conditions and/or developments of the respective tools or components can be taken into consideration.

Similarly, the method step of generating context data can be decoupled in time from the other steps (but does not need to be). As a rule, however, the context data are generated with respect to the respective measurement data when the respective measurement data have been forwarded to the method according to at least one embodiment of the invention or when a post-processing method is to be selected for the respective measurement data.

The term "context data" is understood to cover all data which have a contextual relationship to the respective measurement data. In particular, the context data are allocated out of an acquisition context, a procedure context, an observation context and/or a post-processing context.

The acquisition context, in particular, relates to the type of measurement data acquired, e.g. somatographically/sensorially evoked potentials or in the case of an imaging method nuclear magnetic resonance tomogram of the brain. This can also include data which generally relate to the acquisition of measurement data such as, e.g., the type of acquisition device, the age, other systems connected etc.

The method or procedure context includes in at least one embodiment, in particular, data which relate to the acquisition method and/or the fundamental examination (of the patient). For the aforementioned two examples, these are: somatographically/sensorially evoked potentials, right-hand median nerve or magnetic resonance tomogram of the brain. These can also include data which, e.g., relate to the time of a recording, the duration of the method.

The observation context relates to the observer and the subject observed. Other data can also be acquired here which have also been acquired or observed during the examination.

The post-processing context triggers the type of post-processing which is to be carried out. If, for example, a segmentation of the bronchial tree and volume rendering is to be performed in a computer tomogram, the post-processing context comprises this segmentation and volume rendering respectively.

Overall, all context data which are related to the respective measurement data or can be correlated with these in accordance with different criteria are acquired. In an advantageous alternative embodiment of the invention, not all context data are acquired but only a selection of relevant context data. The selection of context data is formed in such a manner that it is possible to select an optimally designed post-processing method from the set of possible post-processing methods.

After the parsing of the measurement data, together with the context data, and after the evaluation of the data thus parsed, it is possible to automatically determine the type of measurement data acquired. According to at least one embodiment of the invention, this result is placed in context with the registered post-processing components and it is then possible to detect very rapidly and automatically which of the registered post-processing methods are suitable for the respective measurement data present and/or which are optimally designed for these. This can be done, e.g., in the form of a look-up table.

The result of the method according to at least one embodiment of the invention lies in a selection of one or more post-processing methods for the measurement data. The result of the method according to at least one embodiment of the invention is usually displayed. In particular the user receives a proposal for possible post-processing methods via a suitable user interface. If a number of post-processing methods have been selected, it is provided, according to the invention, that these post-processing methods are prioritized in accordance with predeterminable criteria.

It is possible that these prioritization criteria are configurable. In the configuration, the following aspects can be taken into consideration: speed of the method, costs of the proposed post-processing method, existence of alternatives with respect to the respective post-processing method, information content of the respective method, etc. The post-processing methods are then sorted and displayed in accordance with the prioritization criteria. The user interaction enables one of the proposed or selected post-processing methods or several of these to be initiated.

In an example embodiment of the invention, it is provided that a selected post-processing method is automatically initiated. This is the case, in particular, if the method has only selected one post-processing method and there are thus no alternatives for post-processing. This advantageously provides for a user-independent execution of the post-processing.

In principle, the method is designed in such a manner that the selection of one or more post-processing methods takes place for a set of measurement data. However, it is also within the context of at least one embodiment of the invention to select a post-processing method for a group of measurement data or sets of measurement data. This has the advantage that the clinical progress can be improved and accelerated by combining a number of similar measurement data to form a group of measurement data.

In clinical practice, it is frequently necessary to correlate and to combine measurement data of different categories. According to at least one embodiment of the invention it is possible also to process combined sets of measurement data in such a manner that a post-processing method can be automatically selected which is optimally designed for these overall. An example of such a combination consists, for example, in measurement data in the form of image data (for example, PET images) which are to be combined with a selection of laboratory values.

In an example embodiment, the post-processing methods can be subdivided into two rough classes:
1. Visualization methods and
2. Post-processing methods.

The visualization methods are intended for generating a visual representation of the input data. In this connection, for example, tools which transform the measurement data provided into a table, a graph, a diagram, a chart or into a three-dimensional model can be mentioned. In an example embodiment, these visualization methods allow an interaction with the user. It is thus possible to change the visual display of the measurement data, to edit certain data values or to input new data. The user interaction can be made dependant on an authorization of the user.

In the second group of post-processing methods, an output is generated in dependence of the measurement data. This category includes, e.g., statistical methods, evaluation methods, knowledge-based methods for deriving other values for the measurement data, color-coding methods from the field of functional imaging, for example in nuclear magnetic resonance tomograms, etc.

In an example embodiment, these post-processing methods of the second category are not provided with the possibility of user interaction. Thus, the user has no capability of influencing the processing. The result of the post-processing method (or of the post-processing methods in the case of a number of these) is stored in a file especially provided for this purpose, as a rule. It is also possible to store the result of the post-processing immediately and directly in the file in which the measurement data were originally present. In the case of the DICOM SR format, this is the SR tree (i.e. the data structure in this format).

A post-processing method can also include a knowledge-based system which is designed for checking the measurement values acquired. In particular, each measurement value can be checked here for plausibility. It is thus advantageously possible to automatically diagnose measurement value errors. This includes, e.g., artifacts or outliers.

If the measurement data include a diagnosis or a diagnostic report, it is possible by using a knowledge-based system to automatically check the diagnosis associated with the measurement data for plausibility. However, it is also within the context of the invention to specify other checking criteria alternatively or cumulatively in addition to the plausibility check. It is thus possible, for example, to perform a consistency check. In this check, the measurement values acquired are compared with values allocated to them in each case which, for example, are stored in an external database. If differences are found in this case, it is possibly an inconsistent data record. This is displayed to the user. Other checking criteria are also within the context of at least one embodiment of the invention.

In at least one example embodiment of the invention, all method steps are executed automatically. This creates the advantage that even an unskilled user can be offered an optimal post-processing method without additional technical knowledge being necessary. In the alternative embodiments of the invention, individual method steps can be controlled by a user interaction so that the method is semiautomatic overall in this case.

The post-processing methods are usually software-based components. These are connected to the method according to at least one embodiment of the invention or to the device according to at least one embodiment of the invention, respectively, via suitable interfaces.

An alternative solution to the object lies in a method for the post-processing of measurement data, particularly of medical measurement data, which are present in a determinable format, by way of at least one post-processing component, the method comprising the following method steps:

registering post-processing components so that it is defined for each post-processing component on which measurement data it is based, acquiring and/or deriving context data with respect to the measurement data, parsing the measurement data in connection with the acquired or derived associated context data in accordance with the format for the measurement data, evaluating the parsed data in dependence on the registered post-processing components in order to be able to select an optimally designed post-processing method for the measurement data and selecting at least one optimally designed post-processing method for the measurement data, and executing the selected post-processing method(s).

A further alternative solution to the object may reside in a device. With regard to the solution to the object according to the device, the following should be noted:
that which has been said above with respect to the method similarly and correspondingly applies to the device according to at least one embodiment of the invention.

The embodiments of the method according to the invention, described above, can also be formed as computer program products, the computer being caused to carry out the method according to at least one embodiment of the invention, described above, and its program code being executed by a processor.

An alternative solution to the object provides a storage medium which is intended for storing the computer-implemented method described above and can be read by a computer.

In addition, it is possible that individual components of the method described above can be embodied in a sellable unit and the remaining components can be embodied in another sellable unit—as distributive system, as it were. A further solution to the object according to at least one embodiment of the invention therefore lies in a product for selecting at least one post-processing method for the post-processing of measurement data, particularly of medical measurement data, which are present in a predeterminable format, by means of one or more post-processing components, the product comprising:

means for registering post-processing components so that it is defined for each post-processing component what measurement data are required by it as input variable, means for acquiring and/or deriving context data with respect to the measurement data, means for parsing the measurement data in connection with the parsed or derived associated context data in accordance with the format for the measurement data, means for evaluating the parsed data in dependence on the registered post-processing components in order to be able to select at least one optimally designed post-processing method for the measurement data, means for selecting at least one optimally designed post-processing method for the measurement data, the product comprising means which are set up for carrying out those steps of a method in accordance with at least one of the method aspects described above which are effected by the product, wherein at least one further product is set up for carrying out the remaining steps of the method so that all steps of the method are carried out by the interaction of the two products.

BRIEF DESCRIPTION OF THE DRAWINGS

In the following detailed description of the figures, example embodiments, which are not intended to be restrictive, with their features and other advantages are disclosed with referenced to the drawings, in which.

DETAILED DESCRIPTION OF THE EXAMPLE EMBODIMENTS

Figure 1:
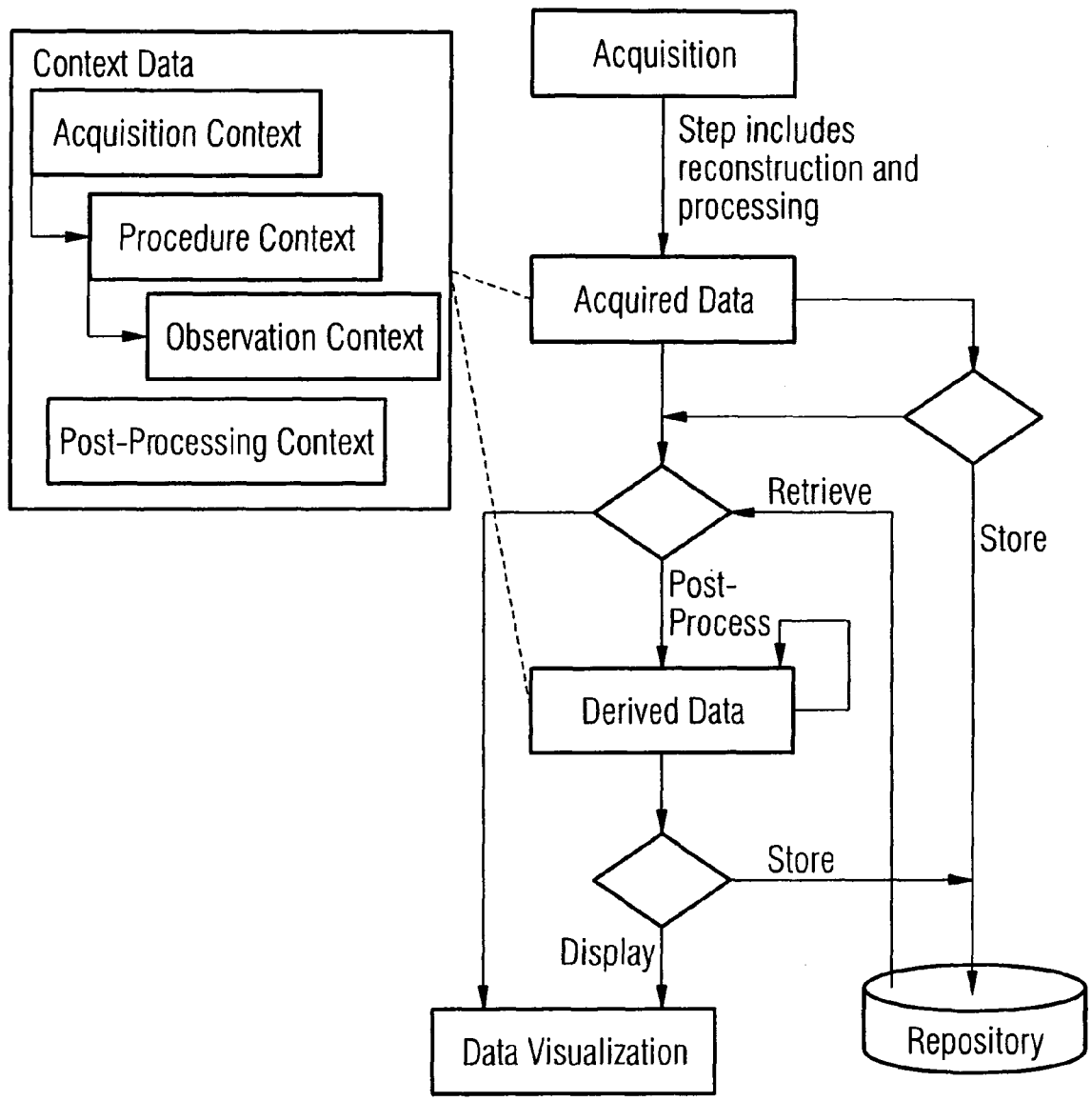
FIG. 1 shows an overview-like representation of a progression according to an example embodiment of the invention.

The main field of application of at least one embodiment of the present invention lies in the medical field and relates in particular to medical/clinical data records. However, it also lies within the context of at least one embodiment of the present invention to apply the principle of this invention to other technical fields such as, e.g., process control or in the field of production technology.

In the field of medical technology, there are in principle many different arrangements by which measurement data MD can be acquired. In the field of functional imaging, these are, in particular, PET (Positron Emission Tomography), and CT (Computer Tomography) or NMR (Nuclear Magnetic Resonance) tomography methods from nuclear medicine. In addition, there are many other fields in which measurement data MD can be acquired. Examples of these are other image data, laboratory results or laboratory values or results from other biological examinations, etc. They all have in common that they are present as measurement values in digital form or are converted into digital form.

As a rule, the measurement data MD are acquired via different types of sensors at the respective devices and are optionally reconstructed or processed, respectively. A reconstruction is mainly used in so-called spiral computer tomograms. The methods of reconstruction and of digital image processing are closely coupled to the image acquisition, in principle, and can be carried out in preceding method steps.

The method steps of post-processing are different from these. In an example embodiment, they are independent of the preprocessing steps in time and/or function. In an example embodiment, therefore, the preprocessing is optional.

In the example described here, the measurement data MD are available in the DICOM SR format. In principle, the format in which the measurement data MD are present can be determined by the user. Thus, it is possible in principle that the user determines other, e.g. XML-encoded formats such as HL7 CDA or CCR documents, apart from the DICOM SR format. In principle, the attributes of the predetermined format (in this case the DICOM format) are mapped onto the attributes and data types of the corresponding format processed by the respective applications.

In the table following, it is shown by way of example how the DICOM format is expanded in accordance with at least one embodiment of the invention. The syntax used is the DICOM-based syntax.

| Attribute Name | Tag | Type | Attribute Description |
|---|---|---|---|
| Measurement Context Code Sequence | (00xx, xxxx) | 3 | Describes the coded measurement context (e.g. the mode of data acquisition) and dimension data |
| > Include 'Code Sequence Macro' Table 8.8-1 | | | No BCID defined |
| > Dimension Sequence | (00xx, xxxx) | 3 | Contains the coded dimension designator and position |
| >> Dimension Code Sequence | (00xx, xxxx) | 1C | Contains the coded dimension designator |
| >> Include 'Code Sequence Macro' Table 8.8-1 | | | No BCID defined |
| >> Position | (00xx, xxxx) | 1C | Position within dimension |

The solution proposed here is based on the DICOM notation. It should be mentioned again at this point that the principle according to the invention is independent of special formats, however. In principle, the measurement data MD should be placed in relation with context data (measurement context code) and/or information how these data are to be mapped into an n-dimensional coordinate system for representation or for any other post-processing.

In principle there are many different, but frequently also many similar possibilities of post-processing measurement data MD. The post-processing takes place in post-processing components K. However, the selection of the optimally designed post-processing method for the respective measurement data MD can cause problems. This is the case, in particular, if there are several possibilities for post-processing.

If, for example, EEG measurement data MD are to be post processed, this requires different post-processing components K than, for example, the post-processing of PET images. In the case of the latter, color coding may be necessary, for example, whereas in the case of the former measurement data a representation or display is to take place. The table reproduced above relates to the case where the measurement data MD are to be subjected to such a post-processing process which indicates or represents the measurement data MD.

In this case, according to at least one embodiment of the invention, the context data are accessed in addition to the measurement data MD to be processed so that it becomes possible to define the two essential parameters for the selection of the type of representation. These are the dimension and position.

In the dimension it is specified what axes of representation are to be used and what units are to be represented on these axes. In the case of the EEG measurement data, a two-dimensional representation is usually selected, the X-axis being the time axis and the Y-axis being the measurement value axis.

The second parameter is the position. This is where the actual mapping of the measurement values takes place. At this point, the measurement values MD acquired are transformed, as it were, into the selected coordinate system. The position at which a measurement value is to be displayed or represented within the selected dimension is determined in concrete terms.

In principle, the measurement data MD present as raw data are transformed in such a manner that they can be processed by the selected post-processing component K. It is then necessary that the method according to the invention can use data or parameters which specify what attributes, data and/or data structures etc. are required by the respective post-processing component. For this reason, according to at least one embodiment of the invention the method step of registering is provided in which the respective post-processing components K, which in principle are, or should be, selectable, are made known to the selection method according to at least one embodiment of the invention. Thus, all post-processing methods or post-processing components K, respectively, are registered with their respective requirements and input variables in the method according to at least one embodiment of the invention and are logged in there.

So that the method according to the invention can carry out the selection of an optimally designed post-processing method, the context data are processed in addition to the pure measurement data MD. In the preferred embodiment, the context information is already provided when a document is generated in which the measurement data are deposited. As shown in the above table, the DICOM format has been correspondingly expanded, so that, apart from the pure measurement data MD, the context information is additionally deposited. The document is thus a DICOM SR document.

In this document, the measurement data MD, any references to external objects and the context data are deposited. Their presence in the format is determined by the user in a preceding method step (in this case as a DICOM SR document).

The selection of at least one optimally designed post-processing method for the measurement data MD is then effected with the aid of the context data and the measurement data MD.

The context data are then adjusted in relation to the respective measurement data MD to the registered parameters of the individual post-processing components K (particularly to the respective prerequisites and requirements of the post-processing component):

what input parameters are processed by the post-processing component,
what type of processing is carried out,
what is the type of post-processing output?

Figure 3:
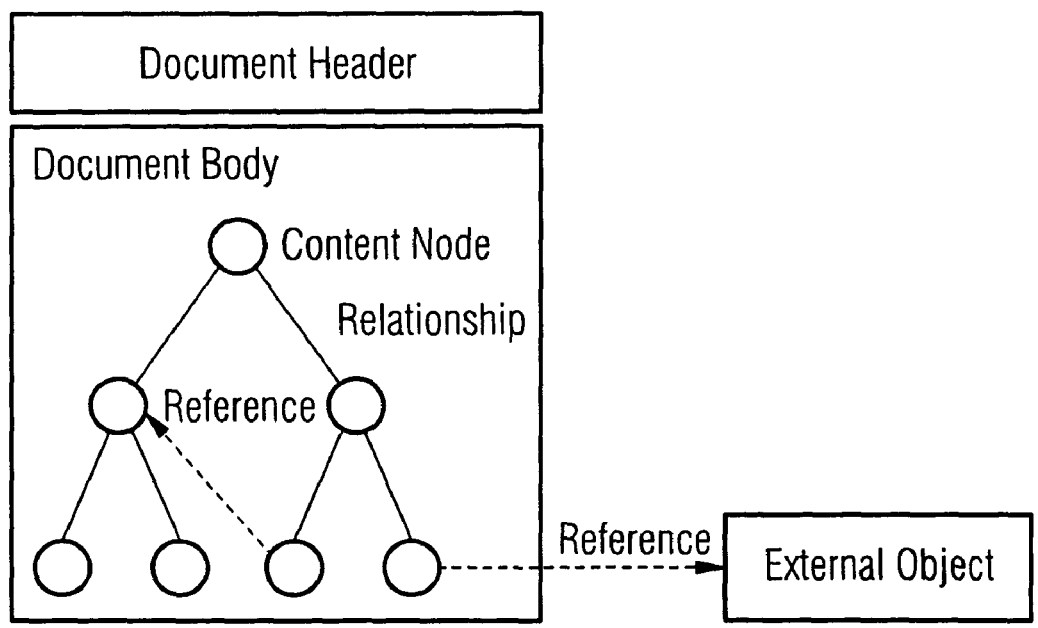
FIG. 3 shows a diagrammatic representation of a data structure, particularly of a structured document with a document header and a document body.

By way of example, FIG. 3 diagrammatically shows a structured document with a header and a body. The header includes metadata with respect to the respective measurement data MD. These can be, for example, the time of day of the acquisition, the acquisition device, etc. The body of the structured document contains the content nodes, the relationships between the respective nodes and a hierarchical structure of the content nodes.

As shown in FIG. 3, it is also possible that a content node points to an external object. For example, the image data supplied by an arrangement can be considered to be an external object. This structured document is generated and therein the context data, which are then supplied to further processing, are deposited in addition to the measurement data MD, according to at least one embodiment of the invention. In an alternative embodiment of the invention, the data (the measurement data MD and the context data) are not deposited in a structured document but in a file in an arbitrary format which comprises the measurement data and the context data.

The method according to at least one embodiment of the invention makes it possible also to collect and jointly process measurement data MD which come from different acquisition sources (CT, PET method, nuclear magnetic resonance, etc.). Thus, a number of measurement data documents can be simultaneously read in, enriched with context data and processed in such a manner that an optimally designed post-processing method can be selected for a group of measurement data.

In an example embodiment of the invention, an actuating mechanism is provided which generates the structured document in which the data are deposited, possibly in combination with referenced image data. In addition, the actuating mechanism writes post-processing data which, in particular, comprise the context data for the measurement data (measurement context code sequence) into the structured document. In addition, it actuates further steps. The further steps include the adjustment of the post-processing information to the registered data for the post-processing components K.

According to at least one embodiment of the invention, so-called plug-ins are provided for this purpose which are used as extension for a document editor or a viewer. In principle there are two classes of plug-ins:

1. Plug-ins for visualization and
2. Plug-ins for any other post-processing.

However, it is also conceivable to provide other types of plug-ins in this case, particularly those which are formed by a knowledge-based system which is designed for evaluating the measurement data MD. In principle, the incorporation and call-up of other external applications is conceivable.

The basic operating sequence according to an example embodiment of the present invention is now to be represented in conjunction with FIG. 1. In a first method step of the acquisition, the measurement data MD are acquired at the respective devices. In this case, the use of any types of sensors is conceivable, particularly image acquisition by the modality detectors in medical imaging methods.

The method step of measurement data acquisition can include reconstruction and preprocessing of the raw data. In a further method step, these measurement data MD are enriched with further context data. Context data can have a reference to structured documents (e.g. to a document node as shown in FIG. 3) or can have a reference to image data (e.g. also to a section of an image data record, some selected images or image data records or layer images).

In addition, it is possible to determine certain regions of an image which are of interest (Region of Interest—ROI) or certain volumes which are of interest (Volume of Interest—VOI). The context data comprise a post-processing context. In addition, an acquisition context is provided which is subdivided into a procedure context and into an observation context.

During the selection of a suitable post-processing method and possibly also during the post-processing, these post-processing context data are used for determining an optimum method for the post-processing and for executing this method. It is essential here that the context data can be changed so that updating of context data is also possible. In addition, the post-processing context data are used for triggering suitable actions, for example a display of overlapping representations (so-called overlays).

Another example lies in the transformation of the raw data to a two- or three-dimensional region of interest (ROI/VOI). Furthermore there are possibilities for post-processing by a knowledge-based system in order to classify interpretations of the user or to check these or to have other processing steps carried out. The knowledge-based system is based on the acquired measurement data MD and on other observations and/or on the context data.

Using the knowledge-based system, it is possible to automatically allocate diagnoses to the respective measurement data MD. In addition, it is possible to check diagnoses which have already been allocated to the measurement data MD at an earlier time and, for example, to indicate comparison values (e.g. values which are within the usual range of values) in order to make the intermeshing of the respective data transparent to the user.

The result of these post-processing steps can be stored in a repository. If the measurement data MD acquired and possibly the enriched measurement data are to be displayed, a data visualization is triggered.

Figure 2:
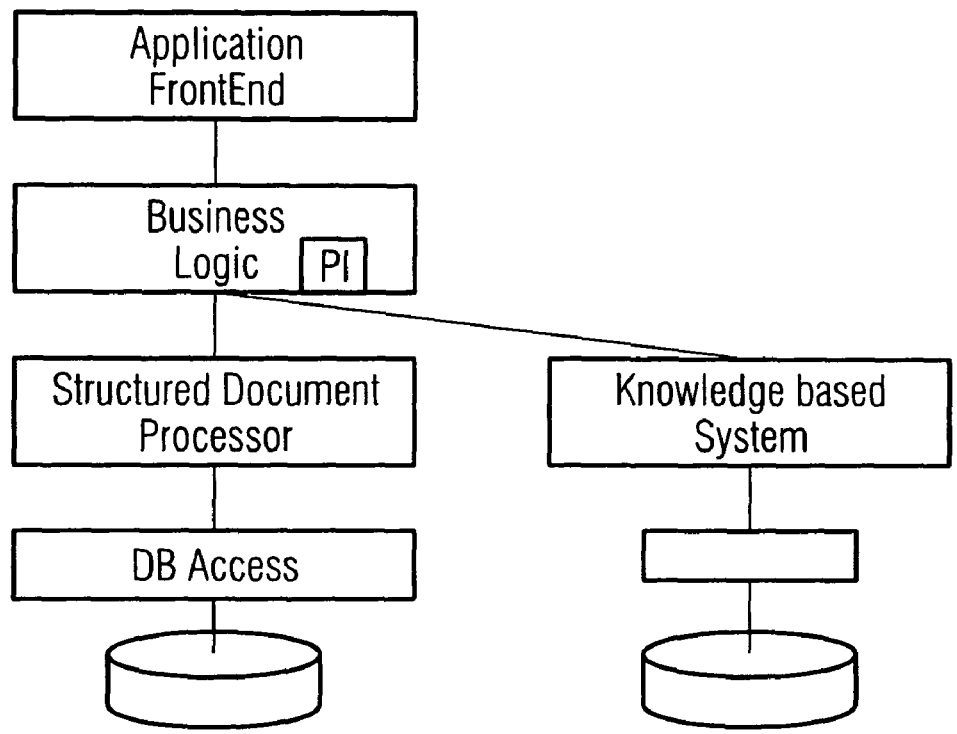
FIG. 2 shows an overview-like representation of an architecture according to an example of the invention.

FIG. 2 describes the fundamental architecture of the solution according to at least one embodiment of the invention. The respective application by means of which the measurement data MD are acquired is the front end. This can be followed by business logic with the aid of which the measurement data MD acquired are processed.

In principle, this can then be followed by a knowledge-based system by means of which the data are classified, checked or otherwise processed as stated above. The result can be stored. By way of the method, a structured document (preferably in the DICOM SR format) is generated into which the measurement data MD, in combination with the post-processing context data, are written. A so-called "SR viewer" or an editor reads out the respective attributes in order to provide for optimum post-processing and/or an optimum display and, if necessary, to trigger further post-processing steps.

Once the structured document has been generated, it is supplied to one or more parsing runs. It is also possible to transform the structured document into another format. Following this, a database access takes place, as a rule. As a result, an optimally selected post-processing method can be determined. The data generated and acquired according to at least one embodiment of the invention can be stored.

Figure 4:
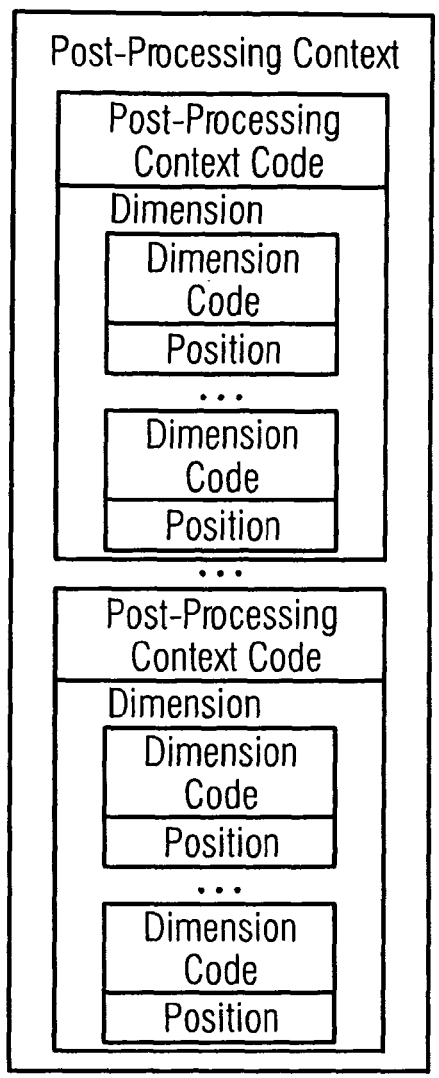
FIG. 4 shows a diagrammatic representation of a data structure according to an example of the invention.

FIG. 4 shows by way of example and as a type of overview a data structure according to an example embodiment of the invention with respect to the post-processing context. The post-processing context includes at least one post-processing context code and optionally dimension data. If there are dimension data present, it should include at least one dimension code and an associated item of position information.

In principle, it is possible that a number of dimension codes and associated positions are present (the dimension being determined via the dimension code). It is possible to use a number of post-processing context codes and dimensions. With the aid of the post-processing context code, it is possible to bring different data records into relation with one another (as already stated above, it is possible to use identical or different codes, which use is based on the application logic used in each case and may require different context data).

The essential modules of an example device according to at least one embodiment of the invention are to be described in connection with FIG. 5.

To be able to acquire the parameters and prerequisites of the post-processing component K a registration module 10 is provided which reads in the respective parameters and data, via an interface, if necessary. The raw data acquired from the respective devices (X-ray device, CT, etc.) can be read in—also via an interface, if necessary—and are supplied to a context module 12.

According to at least one embodiment of the invention, other data apart from the pure measurement data MD, particularly context data, are processed. The other data can be present in a form already acquired, transferred from other modules or calculated or derived by the method according to at least one embodiment of the invention. As a rule, this occurs automatically.

Figure 5:
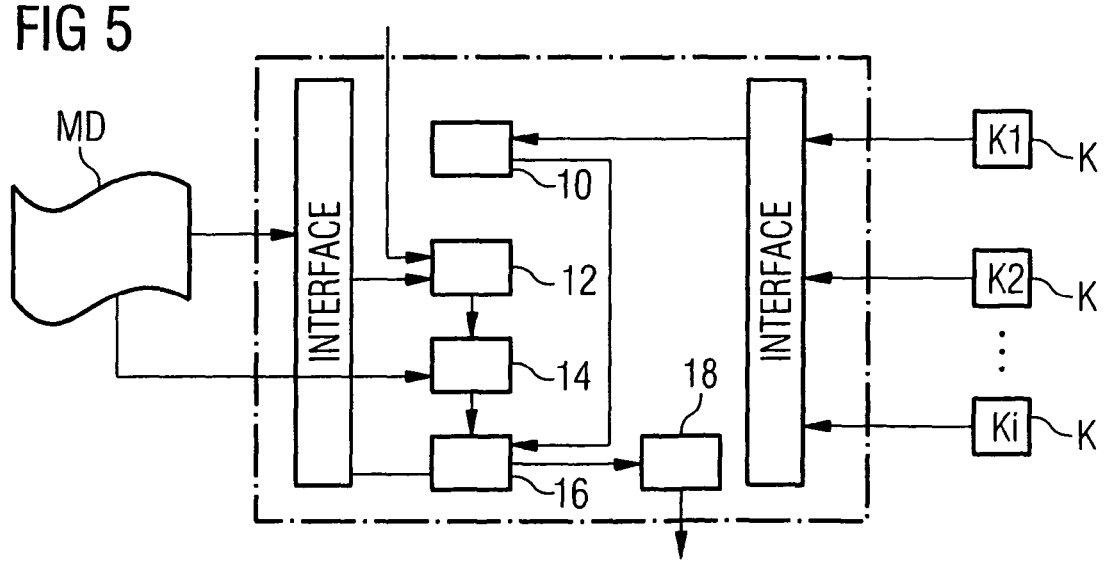
FIG. 5 shows an overview-like representation of essential modules of a device according to an example of the invention.

The arrow pointing out the context module 12 from the top on the outside in FIG. 5 is intended to illustrate that other data are supplied, particularly context data. At this point, the structured document is thus generated in which, apart from the measurement data MD, associated context data are stored. The structured document is supplied to a parser 14. The parser 14 looks for data enabling the suitable post-processing method to be evaluated or to be selected in the structured document according to configurable criteria.

The data parsed by the parser 14 are then supplied to an evaluating module 16 which is used for adjusting the measurement data MD present on one side and the enriched context data to the data present on the other side which have been acquired with the registration module 10 with respect to the post-processing component K. Thus, the evaluating module 16 is used for selecting one or more suitable post-processing methods for the respective measurement data MD.

The result of the method can be a proposal which is displayed to the user via a suitable user interface. It is possible in this arrangement to automatically and directly trigger the activation of the selected post-processing component K. In an alternative embodiment, it is possible to not directly trigger the selected and proposed post-processing component K but to make this dependent on a user interaction. In the latter case, the user can check the proposal and has intervention capabilities, particularly for selecting a particular post-processing method if others have been proposed.

The result of the method according to at least one embodiment of the invention is usually stored and/or displayed. This is marked by the arrow pointing downwards from the selection module 18. The dot-dashed line around the modules 10, 12, 14, 16 and 18 around the respective interfaces is intended to mark that, in principle, the system can be expanded and other applications can be connected.

It is also possible that the evaluating module 16 writes the result of the selection method directly into the structured document MD. In an alternative embodiment of the invention it is provided that the result is stored in another file.

In the text which follows, the content of the respective context data is to be shown by way of example with the example of functional imaging. In particular, the basis for the acquired data MD is a nuclear magnetic resonance tomography of the brain.

| | |
|---|---|
| Acquisition context: | functional imaging, nuclear magnetic resonance tomography of the brain |
| Procedure context: | nuclear magnetic resonance tomography of the brain |
| Post-processing context: | functional evaluation, left-hand somatographic/sensorial cortex |
| Stimulus: | pressing the finger on the right hand. |

As a further example, the content of the respective context data which can be acquired in relationship with evoked potentials shall be listed in the text which follows:

| | |
|---|---|
| Acquisition context: | somatographically/sensorially evoked potentials |
| Procedure context: | somatographically/sensorially evoked potentials, right-hand median nerve |
| Post-processing context: | functional evaluation, left-hand somatographic/sensorial cortex and afferent nerves (all post-processing data exist in the structured document and can refer to associated images of |

| | |
|---|---|
| | external objects. It is also possible to allocate a post-processing context to a referenced image. The structured document also comprises the evoked potentials and, respectively, the derivations and measurements of the potentials. |
| Measurement context code: | Functional MRI imaging (blood circulation), unit, value, dimension (X, Y, Z) with position information (mapped onto MRI slices). |

By way of the method according to at least one embodiment of the invention it is possible, e.g., to combine MRI spectroscopy (as a type of measurement data) and a genetic analysis (as another type of measurement data) by superimposing these on magnetic resonance images and bringing them into relation, to form a genetic expression (e.g. p53) and/or a biologically funded growth factor (e.g. epidermal growth factor).

In principle, the device according to at least one embodiment of the invention, particularly the evaluating module 16, comprises a number of plug-ins. The plug-ins are used for the post-processing of the measurement data MD acquired. In principle, it is possible to register further plug-ins at any time and supply them to the device or the method, respectively. Each plug-in is equipped with corresponding interfaces in order to be able to transform the data.

Preferably, a plug-in for visualization is provided which is used for the visual representation of the data, the change in the data and the input of new data.

In addition, a plug-in for further processing is provided which makes it possible to derive output data from the input data (the measurement data MD). It is not provided for a user interaction to take place. The result or results of the processing of the respective plug-in is/are usually stored back into the SR tree.

In the method according to at least one embodiment of the invention, the respective plug-in is dynamically loaded and it is determined which measurement contexts are supported by the plug-in. This is made possible by the interface. The correlation between measurement context and the respective plug-ins is kept and stored in a plug-in registry. It is possible to define a priority for each plug-in so that it is possible to select a post-processing method if several post-processing methods are possible and fit the respective measurement context.

In an example embodiment, the method is designed in such a manner that navigating through the structured document is carried out via the SR tree. As soon as a measurement context has been found, all plug-ins are called up which are found in the plug-in registry and which support the measurement context. The implementation of the plug-in interface for processing the data from the structured report (from the structured document) can be designed in such a manner that it includes the following modes:

Read Only:

The data of the structured document generated are only read, no output is generated. A typical example of this is a user display.

Processing:

The data of the structured document are processed further for generating a result which is stored. A typical example of this is a plug-in for decision support which evaluates the data (particularly the measurement context data) and stores the result, e.g. in a database.

Editing:

The data of the structured document are processed and written back into the SR tree as modification or addition. A typical example of this is a plug-in which enables the user to interact with the data and to change the existing data or to add new data.

In principle it is necessary for each plug-in to have at least one interface for processing the data of the structured document. In one embodiment of the interface, the plug-in receives as argument the part-tree of the structured document which hangs on the current context node (that is to say where the measurement context is positioned). In another alternative embodiment of the interface, the plug-in receives as argument a reference or an identity of the current context node (that is to say where the measurement context is positioned) and additionally a reference to the entire SR tree. The term "SR" refers to the structured document and the term "SR tree" refers to the tree, shown as an overview in FIG. 3, as the data structure of the structured document.

Finally, it shall be pointed out that the description of the invention and the example embodiments, in principle, should not be understood to be restrictive with regard to a particular physical implementation of the invention. In particular, it is clear to the relevant expert that embodiments of the invention can be implemented partially or completely in software and/or hardware and/or distributed over a number of physical products—including, in particular, computer program products.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for selecting at least one post-processing method for post-processing measurement data, particularly medical measurement present in a format, the method comprising:

registering, using a first processor, post-processing components to define, for each post-processing component, measurement data upon which post-processing components are based;

acquiring context data, using a second processor, with respect to the measurement data;

automatically parsing, using a third processor, the measurement data in connection with the acquired context data in accordance with the format for the measurement data; and automatically evaluating, using a fourth processor, the parsed data in dependence on the registered post-processing components, to select the at least one post-processing method which is optimally designed for the measurement data; and automatically selecting the at least one post-processing method for the measurement data, wherein a plurality of measurement data is collected and jointly processed from a plurality of different acquisition sources, and wherein the plurality of different measurement data from the plurality of different acquisition sources are simultaneously read in, parsed with context data and jointly processed to select the at least one post-processing method for a group of measurement data of the plurality of measurement data.

2. The method as claimed in claim 1, further comprising at least one of:

displaying at least one proposal for a selected post-processing method; and triggering the selected post-processing method with the data.

3. The method as claimed in claim 1, wherein the measurement data are read in via interfaces to at least one sensorial measurement.

4. The method as claimed in claim 1, wherein the measurement data are acquired as part of functional imaging or present in a structured document.

5. The method as claimed in claim 1, wherein the measurement data include at least one of image data, measurement values, laboratory findings and other measurement data.

6. The method as claimed in claim 1, wherein the context data includes data that is allocated to at least one of an acquisition context, a procedure context, an observation context and a post-processing context.

7. The method as claimed in claim 1, wherein the post-processing method includes at least one of method for at least one of displaying and presenting measurement data; method for further evaluation of the measurement data; and method for checking the measurement data.

8. The method as claimed in claim 1, wherein the data used for the selection are displayed or stored in a file.

9. The method as claimed in claim 1, wherein the measurement data are acquired as part of functional imaging or present in a format which is based on at least one of DICOM, HL 7 CDS and ASTM CCR Standards.

10. A device for post-processing of measurement data present in a format, comprising:

at least one registration module, including a first processor, configured to register post-processing components to define, for each post-processing component, a type of measurement data required as input;

at least one context module, including a second processor, configured to acquire and derive context data with respect to the measurement data;

at least one parser, including a third processor, configured to automatically parse the measurement data in connection with the acquired context data in accordance with the format for the measurement data; and at least one evaluating module, including a fourth processor, configured to automatically evaluate the data parsed with the parser in dependence on the post-processing components registered with the registration module to automatically select a post-processing component for the measurement data, wherein a plurality of measurement data is collected and jointly processed from a plurality of different acquisition sources, and wherein the plurality of different measurement data from the plurality of different acquisition sources are simultaneously read in, parsed with context data and jointly processed to select the at least one post-processing method for a group of measurement data of the plurality of measurement data.

11. The device as claimed in claim 10, further comprising at least one selection module to select at least one optimally designed post-processing component for the measurement data.

12. A non-transitory computer readable medium including program segments for, when executed on a computer, causing the computer to carry out a method for selecting at least one post-processing method for post-processing measurement data, the method comprising:

registering, using a first processor, post-processing components to define, for each post-processing component, measurement data upon which post-processing components are based;

acquiring context data, using a second processor, with respect to the measurement data;

automatically parsing, using a third processor, the measurement data in connection with the acquired context data in accordance with the format for the measurement data; and automatically evaluating, using a fourth processor, the parsed data in dependence on the registered post-processing components, to select the at least one post-processing method which is optimally designed for the measurement data; and automatically selecting the at least one post-processing method for the measurement data, wherein a plurality of measurement data is collected and jointly processed from a plurality of different acquisition sources, and wherein the plurality of different measurement data from the plurality of different acquisition sources are simultaneously read in, parsed with context data and jointly processed to select the at least one post-processing method for a group of measurement data of the plurality of measurement data.

* * * * *